United States Patent
Oh et al.

(10) Patent No.: US 7,745,419 B2
(45) Date of Patent: Jun. 29, 2010

(54) PHARMACEUTICAL COMPOSITION FOR TREATING CANCER

(75) Inventors: Yu-Kyoung Oh, Seoul (KR); Ga Yong Shim, Yongin-si (KR); Sang-Hee Kim, Yangsan-si (KR)

(73) Assignee: Korea University Industrial & Academic Collaboration Foundation, Seoul (KR)

( * ) Notice: Subject to any disclaimer, the term of this patent is extended or adjusted under 35 U.S.C. 154(b) by 0 days.

(21) Appl. No.: 12/234,271

(22) Filed: Sep. 19, 2008

(65) Prior Publication Data

US 2009/0081282 A1 Mar. 26, 2009

(30) Foreign Application Priority Data

Sep. 21, 2007 (KR) ...................... 10-2007-0096396

(51) Int. Cl.
*C07H 21/02* (2006.01)
*C07H 21/04* (2006.01)
*A61K 31/70* (2006.01)

(52) U.S. Cl. ...................... 514/44; 536/23.1; 536/24.3; 536/24.33; 536/24.5

(58) Field of Classification Search .................... 514/44
See application file for complete search history.

(56) References Cited

U.S. PATENT DOCUMENTS

2004/0247593 A1   12/2004   He et al.

OTHER PUBLICATIONS

Nguyen et al. (Current Opinion in Molecular Therapeutics, 2008 vol. 10(2):158-167.*
Lu et al. (2005) in RNA Interference Technology (Cambridge, Appasani, ed.).*
Samarsky et al. in RNA Interference Technology, (2005) (Cambridge, Appasani, ed.) pp. 389-394.*
Downward, J. (BMJ, 2004 vol. 328:1245-1428).*

* cited by examiner

*Primary Examiner*—Sean McGarry
*Assistant Examiner*—Terra Cotta Gibbs
(74) *Attorney, Agent, or Firm*—Rothwell, Figg, Ernst & Manbeck, P.C.

(57) ABSTRACT

The present invention provides a small interfering RNA (siRNA) that is capable of inhibiting intracellular expression of Wnt1 through complementary binding to a Wnt1 transcript (mRNA transcript) base sequence and a pharmaceutical composition for treating cancer comprising the same. siRNA of the present invention which is complementary to a base sequence of a Wnt1 transcript (mRNA) provides apoptotic cancer cell death due to inhibition of expression of Wnt1 commonly expressed in cancer cells, by RNA-mediated interference (RNAi). Therefore, the composition of the present invention comprising the same can be used as an excellent anticancer drug.

13 Claims, 4 Drawing Sheets

SEQUENCE LISTING

<160> NUMBER OF SEQ ID NOS: 49

<210> SEQ ID NO 1
<211> LENGTH: 19
<212> TYPE: DNA
<213> ORGANISM: Homo sapiens

<400> SEQUENCE: 1
ccacgaacct gcttacaga                                                19

<210> SEQ ID NO 2
<211> LENGTH: 19
<212> TYPE: DNA
<213> ORGANISM: Homo sapiens

<400> SEQUENCE: 2
cctgcttaca gactccaag                                                19

<210> SEQ ID NO 3
<211> LENGTH: 19
<212> TYPE: DNA
<213> ORGANISM: Homo sapiens

<400> SEQUENCE: 3
caaacagcgg cgtctgata                                                19

<210> SEQ ID NO 4
<211> LENGTH: 19
<212> TYPE: DNA
<213> ORGANISM: Homo sapiens

<400> SEQUENCE: 4
aaccgaggct gtcgagaaa                                                19

<210> SEQ ID NO 5
<211> LENGTH: 19
<212> TYPE: DNA
<213> ORGANISM: Homo sapiens

<400> SEQUENCE: 5
tgtcgagaaa cggcgttta                                                19

<210> SEQ ID NO 6
<211> LENGTH: 19
<212> TYPE: DNA
<213> ORGANISM: Homo sapiens

<400> SEQUENCE: 6
tcgagaaacg gcgtttatc                                                19

<210> SEQ ID NO 7
<211> LENGTH: 19
<212> TYPE: DNA
<213> ORGANISM: Homo sapiens

<400> SEQUENCE: 7
cggcgtttat cttcgctat                                                19

<210> SEQ ID NO 8
<211> LENGTH: 19
<212> TYPE: DNA
<213> ORGANISM: Homo sapiens

-continued

```
<400> SEQUENCE: 8
tcagaaggtt ccatcgaat                                               19

<210> SEQ ID NO 9
<211> LENGTH: 19
<212> TYPE: DNA
<213> ORGANISM: Homo sapiens

<400> SEQUENCE: 9
acctgttgac ggattccaa                                               19

<210> SEQ ID NO 10
<211> LENGTH: 19
<212> TYPE: DNA
<213> ORGANISM: Homo sapiens

<400> SEQUENCE: 10
cagcgacaac attgacttc                                               19

<210> SEQ ID NO 11
<211> LENGTH: 19
<212> TYPE: DNA
<213> ORGANISM: Homo sapiens

<400> SEQUENCE: 11
tcctcatgaa ccttcacaa                                               19

<210> SEQ ID NO 12
<211> LENGTH: 19
<212> TYPE: DNA
<213> ORGANISM: Homo sapiens

<400> SEQUENCE: 12
gtacgaccgt attctccaa                                               19

<210> SEQ ID NO 13
<211> LENGTH: 19
<212> TYPE: DNA
<213> ORGANISM: Homo sapiens

<400> SEQUENCE: 13
gagaaatcgc ccaacttct                                               19

<210> SEQ ID NO 14
<211> LENGTH: 19
<212> TYPE: DNA
<213> ORGANISM: Homo sapiens

<400> SEQUENCE: 14
atcgcccaac ttctgcacg                                               19

<210> SEQ ID NO 15
<211> LENGTH: 19
<212> TYPE: DNA
<213> ORGANISM: Homo sapiens

<400> SEQUENCE: 15
aactgcacgc acgcgcgta                                               19

<210> SEQ ID NO 16
<211> LENGTH: 21
<212> TYPE: RNA
```

```
<213> ORGANISM: Artificial Sequence
<220> FEATURE:
<223> OTHER INFORMATION: siRNA against Wnt1, sense sequence

<400> SEQUENCE: 16
ccacgaaccu gcuuacagau u                                               21

<210> SEQ ID NO 17
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 17
ucuguaagca gguucguggu u                                               21

<210> SEQ ID NO 18
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 18
ccugcuuaca gacuccaagu u                                               21

<210> SEQ ID NO 19
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 19
cuuggagucu guaagcaggu u                                               21

<210> SEQ ID NO 20
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 20
caaacagcgg cgucugauau u                                               21

<210> SEQ ID NO 21
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 21
uaucagacgc cgcuguuugu u                                               21

<210> SEQ ID NO 22
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 22
aaccgaggcu gucgagaaau u                                               21
```

<210> SEQ ID NO 23
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 23
uuucucgaca gccucgguuu u                                              21

<210> SEQ ID NO 24
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 24
ugucgagaaa cggcguuuau u                                              21

<210> SEQ ID NO 25
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 25
uaaacgccgu uucucgacau u                                              21

<210> SEQ ID NO 26
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 26
ucgagaaacg gcguuuaucu u                                              21

<210> SEQ ID NO 27
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 27
gauaaacgcc guuucucgau u                                              21

<210> SEQ ID NO 28
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 28
cggcguuuau cuucgcuauu u                                              21

<210> SEQ ID NO 29
<211> LENGTH: 21
<212> TYPE: RNA
<213> ORGANISM: Artificial Sequence
<220> FEATURE:

<223> OTHER INFORMATION: siRNA against Wnt1, antisense sequence

<400> SEQUENCE: 29
auagcgaaga uaaacgccgu u                                                     21

<210> SEQ ID NO 30
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 30
ucagaagguu ccaucgaauu u                                                     21

<210> SEQ ID NO 31
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 31
auucgaugga accuucugau u                                                     21

<210> SEQ ID NO 32
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 32 accguugac ggauccaau u                                                       21

<210> SEQ ID NO 33
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 33
uuggaauccg ucaacagguu u                                                     21

<210> SEQ ID NO 34
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 34
cagcgacaac auugacuucu u                                                     21

<210> SEQ ID NO 35
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 35
gaagucaaug uugucgcugu u                                                     21

```
<210> SEQ ID NO 36
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 36
uccucaugaa ccuucacaau u                                              21

<210> SEQ ID NO 37
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 37
uugugaaggu ucaugaggau u                                              21

<210> SEQ ID NO 38
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 38
guacgaccgu auucuccaau u                                              21

<210> SEQ ID NO 39
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 39
uuggagaaua cggucguagu u                                              21

<210> SEQ ID NO 40
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 40
gagaaaucgc ccaacuucuu u                                              21

<210> SEQ ID NO 41
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 41
agaaguuggg cgauuucucu u                                              21

<210> SEQ ID NO 42
<211> LENGTH: 21
<212> TYPE: RNA
<213> ORGANISM: Artificial Sequence
<220> FEATURE:
<223> OTHER INFORMATION: siRNA against Wnt1, sense sequence
```

```
<400> SEQUENCE: 42
aucgcccaac uucugcacgu u                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 43
cgugcagaag uugggcgauu u                                              21

<210> SEQ ID NO 44
<211> LENGTH: 21
<212> TYPE: RNA
<213> ORGANISM: Artificial Sequence
<220> FEATURE:
<223> OTHER INFORMATION: siRNA against Wnt1, sense sequence

<400> SEQUENCE: 44
aacugcacgc acgcgcguau u                                              21

<210> SEQ ID NO 45
<211> LENGTH: 21
<212> TYPE: RNA
<213> ORGANISM: Artificial Sequence
<220> FEATURE:
<223> OTHER INFORMATION: siRNA against Wnt1, antisense sequence

<400> SEQUENCE: 45
uacgcgcgug cgugcaguuu u                                              21

<210> SEQ ID NO 46
<211> LENGTH: 21
<212> TYPE: DNA
<213> ORGANISM: Artificial Sequence
<220> FEATURE:
<223> OTHER INFORMATION: luciferase GL2 experssion-inhibiting siRNA

<400> SEQUENCE: 46
cguacgcgga auacuucgat t                                              21

<210> SEQ ID NO 47
<211> LENGTH: 21
<212> TYPE: DNA
<213> ORGANISM: Artificial Sequence
<220> FEATURE:
<223> OTHER INFORMATION: luciferase GL2 expression-inhibiting siRNA

<400> SEQUENCE: 47
ucgaaguauu ccgcguacgt t                                              21

<210> SEQ ID NO 48
<211> LENGTH: 20
<212> TYPE: DNA
<213> ORGANISM: Artificial Sequence
<220> FEATURE:
<223> OTHER INFORMATION: Wnt1-specific primer

<400> SEQUENCE: 48
cggcgtttat cttcgctatc                                                20

<210> SEQ ID NO 49
<211> LENGTH: 20
```

```
<212> TYPE: DNA
<213> ORGANISM: Artificial Sequence
<220> FEATURE:
<223> OTHER INFORMATION: Wnt1-specific primer

<400> SEQUENCE: 49
gcctcgttgt tgtgaaggtt                                           20
```

PHARMACEUTICAL COMPOSITION FOR TREATING CANCER

CROSS REFERENCE TO RELATED APPLICATIONS

This application claims priority from Korean patent application No. 10-2007-0096396 filed on Sep. 21, 2007, all of which is incorporated herein by reference in its entirety for all purposes.

TECHNICAL FIELD

The present invention relates to a small interfering RNA (siRNA) that complementarily binds to a Wnt1 transcript (mRNA transcript) base sequence to thereby inhibit intracellular expression of Wnt1 and a pharmaceutical composition for treating cancer comprising the same.

BACKGROUND ART

Wnt is a secreted protein that binds to surface receptors of neighboring cells to regulate the expression of various genes. The Wnt gene family was found ubiquitously in various types of tumors and was given a name "int" as the first cellular oncogene. Since then, it was found that a wingless gene implicated in the metamorphosis of *Drosophila* species is a homolog of the gene int-1 and therefore it was also suggested that the int gene will play a crucial role in the embryogenesis of *Drosophila* species. Accordingly, the name Wnt was coined as a combination of Wg (wingless) and Int.

The Wnt signaling pathway has been recognized as a key pathway responsible for oncogenesis. A member of the Wnt signaling pathway, such as adenomatous polyposis coli (APC), Axin, Axin2, βTrCP (E3 ligase), or the like, that binds to β-catenin to form an inactivated complex, may undergo mutagenesis incapable of degrading β-catenin and β-catenin may also be mutated to a non-degradable form, which leads to increased nuclear β-catenin accumulation, finally resulting in activation of the Wnt/β-catenin pathway. High nuclear accumulation of β-catenin leads to formation of a complex of β-catenin with T-cell factor/Lymphoid enhancing factor (TCF/LEF), which consequently results in induction of transcription of target genes.

Activation of the Wnt/β-catenin pathway is known to elicit regulated expression of numerous genes involved in carcinogenesis. The Wnt/β-catenin pathway induces expression of c-myc and cyclin D1 to thereby activate cell division, and also induces expression of a growth factor receptor, c-met and a growth factor, fibroblast growth factor 18 (FGF 18) to thereby increase cell proliferation. Further, it increases expression of anti-apoptotic proteins such as survivin protein as well as proteins necessary for cell proliferation, and induces expression of a vascular endothelial growth factor (VEGF) gene to stimulate tumor angiogenesis and provide a foundation for tumor growth and metastasis. In addition, for migration and metastasis of cancer cells, APC stimulated exchange factor (ASEF), matrix metalloproteinase (MMP) family, CD44 and the like, which are correlated with cell adhesion and extracellular matrix, function as target proteins of the Wnt/β-catenin pathway. A great deal of research and study has been actively attempted on development of an antitumor agent that is intended to target the Wnt/β-catenin pathway implicated in regulation of a variety of carcinogenesis-related proteins as described above. Unfortunately, most of such approaches made up to date are pathway inhibitors using chemical synthetic drugs which are designed based on a tertiary structure of individual proteins implicated in the Wnt/β-catenin pathway (Nick et al., Nature Reviews Drug Discovery, 5:997-1014, 2006).

RNA-mediated interference (RNAi) is a phenomenon wherein a 21-25 nucleotide-long double stranded siRNA specifically binds to a transcript (mRNA transcript) having a complementary sequence and degrades the corresponding transcript to thereby inhibit expression of a target protein of interest. As the RNA-mediated interference has recently suggested the solution to the problems encountered in development of conventional chemical synthetic drugs, many efforts have been made on development of various therapeutic agents, particularly antitumor agents, through selective inhibition of the expression of a certain protein at the transcript level. Production of target-directed small-molecule chemical drugs takes a long development period of time and tremendous development costs until they are optimized to certain protein targets, whereas the most pronounced advantage of siRNA drugs using the RNA-mediated interference phenomenon is in that it readily enables development of the optimized lead compounds for all the protein targets including non-druggable target substances. Protein or antibody drugs suffer from difficulties of production thereof due to complicated manufacturing processes, whereas siRNAs have significant advantages such as ease of synthesis, separation and purification, consequently relatively easy and convenient commercial-scale production, higher storage stability attributed to intrinsic nature of nucleic acid materials, as compared to protein drugs, and the like. Further, siRNA-based drugs are receiving a great deal of interest as a novel drug candidate group, based on a variety of strengths such as specific molecular target-directed antagonism, unlike conventional drugs (David et al., Nature Chemical Biology, 2:711-719, 2006).

The primary challenge associated with siRNA-based therapy is the identification of the optimum sequence where siRNA has the highest activity in the target base sequence. It is known that the efficiency of RNA-mediated interference is significantly affected by a specific binding site to the target transcript. Based on the database accumulated for the past several years, algorithms have been developed which are capable of designing a sequence position of siRNA substantially inhibiting expression of the target RNA, instead of simply binding to the transcript, and are currently available to users. However, it cannot be said that all of siRNAs determined by an in silico method using computer algorithms can effectively inhibit target RNAs in real cells and in vivo. Further, it is known that even when requirements necessary for complementary binding of siRNA to the target transcript are satisfied, the stability and intracellular location of RNAs and proteins, the state of proteins implicated in RNA-mediated interference, and a variety of other unknown factors are implicated in the determination of RNA-mediated interference efficiency. To this end, there is a need for development of a technique which will be carried out for a target protein by selecting several target sequence positions per transcript of one gene, preparing the corresponding siRNAs and screening an optimum position sequence having high expression-inhibitory activity from among such a candidate group (Derek et al., Annual Review of Biomedical Engineering, 8:377-402, 2006).

DISCLOSURE OF THE INVENTION

Technical Problem

Therefore, the present invention has been made in view of the above problems, and it is an object of the present invention to provide small interfering RNAs (siRNAs) that complementarily bind to a Wnt1 transcript base sequence to thereby inhibit intracellular expression of Wnt1 and a pharmaceutical composition for treating cancer comprising the same.

Technical Solution

The present invention provides a pharmaceutical composition for treating cancer comprising one or more small interfering RNAs (siRNAs) that are capable of inhibiting intracellular expression of Wnt1 through complementary binding to a Wnt1 transcript (mRNA transcript) base sequence as set forth in SEQ ID NO: 2 (5'-CCTGCTTACAGACTCCAAG-3'), SEQ ID NO: 7 (5'-CGGCGTTTATCTTCGCTAT-3') or SEQ ID NO: 14 (5'-ATCGCCCAACTTCTGCACG-3').

The pharmaceutical composition for treating cancer comprising Wnt1 expression-inhibiting siRNA in accordance with the present invention may comprise one siRNA such that it can bind only to a single sequence position of the transcript (mRNA) of Wnt or otherwise may comprise two or more siRNAs such that one or more sequence positions of the Wnt transcript can be targeted.

As used herein, the term "siRNA" is intended to encompass chemically modified siRNA molecules designed to prevent rapid degradation that may occur by the action of in vivo nucleases. Those skilled in the art will appreciate that it is possible to synthesize and modify siRNA molecules as desired, using any conventional method known in the art (see Andreas Henschel, Frank Buchholzl and Bianca Habermann (2004) DEQOR: a web-based tool for the design and quality control of siRNAs. Nucleic Acids Research 32 (Web Server Issue):W113-W120). siRNA has a double-stranded structure, and therefore is relatively stable as compared to single-stranded ribonucleic acid or antisense oligonucleotide molecules. However, siRNA is readily susceptible to in vivo nuclease degradation, so it is possible to lower a degradation rate of siRNA via chemical modification thereof. Chemical modification of siRNA to secure that siRNA is chemically stable and resistant against rapid degradation may be carried out by any conventional method well known to those skilled in the art. The most conventional method used in chemical modification of siRNA is boranophosphate or phosphorothioate modification. These materials form stable nucleoside-nucleoside association of siRNA molecules, thereby conferring resistance to nucleic acid degradation. Even though it is resistant to nucleic acid degradation, the boranophosphate-modified ribonucleic acid is not synthesized by a chemical reaction and is synthesized only by incorporation of boranophosphate into ribonucleic acid via in vitro transcription. The boranophosphate modification is a relatively easy method, but has a disadvantage associated with difficulty of site-directed modification at a certain position of target molecules or compounds. On the other hand, the phosphorothioate modification is advantageous for introduction of sulfur elements into a desired site, but excessive phosphothioation may result in problems associated with decreased efficiency, toxicity, and formation of non-specific RNA-induced silencing complex (RISC). For these reasons suffered by the above-mentioned two modification methods, it may be preferred to employ a method which is designed to provide nuclease resistance via introduction of chemical modification only at a termination position of ribonucleic acid (a region beyond 3'-terminal). Further, chemical modification of a ribose ring is also known to enhance the nuclease resistance of nucleic acid. Particularly, modification at 2'-position of the ribose which is present in cells leads to stabilization of siRNA molecules. However, the stability of siRNA molecules increases only with correct introduction of a methyl group into the above-specified position of the ribose ring. Further, introduction of excessively large numbers of methyl groups may adversely result in loss of ribonucleic acid-mediated interference. Chemical modifications may also be made to improve the in vivo pharmacokinetic retention time and efficiency (Mark et al., Molecular Therapy, 13:644-670, 2006).

In addition to chemical modifications, a safe and efficient delivery system is still required to increase intracellular delivery efficiency of siRNA molecules. For this purpose, siRNA of the present invention may be incorporated in the form of a complex with a nucleic acid delivery system into a pharmaceutical composition for treating cancer.

The nucleic acid delivery system for intracellular delivery of nucleic acid materials may be broadly divided into a viral vector system and a non-viral vector system. The most conventionally and widely used system is a viral vector system because it provides a high delivery efficiency and a long retention time in vivo. Among a variety of viral vectors, a retroviral vector, an adenoviral vector, an adeno-associated viral vector, and the like are widely employed. These viral vector systems are efficient in intracellular delivery of ribonucleic acid, but suffer from various problems associated with safety concerns, such as difficulty of recombination of the ribonucleic acid into a virus having in vivo activity, elicitation of immune response, undesirable random insertion of the ribonucleic acid into host chromosomes, and the like. On the other hand, the non-viral vector system exhibits various advantages, such as low toxicity and immune response, feasibility of repeated administration, convenient formation of a complex of the delivery system with ribonucleic acid, and easy industrial-scale production, as compared to the viral vector system. Further, organ/cell-targeted delivery of nucleic acid to affected cells or tissue lesions can be carried out by conjugation of a specific ligand with the non-viral vector. Examples of the non-viral vector that can be used in the present invention may include various formulations such as liposomes, cationic polymers, micelles, emulsions, nanoparticles, and the like. The nucleic acid delivery system can significantly enhance delivery efficiency of the desired nucleic acid into animal cells and can deliver nucleic acids into any type of animal cells, depending upon the desired uses and applications of the nucleic acids.

In one embodiment of the present invention, the nucleic acid delivery system may be a cationic liposome.

Examples of the cationic liposome may include, but are not limited to, at least one cationic lipid selected from the group consisting of 1,2-dioleoyl-sn-glycero-3-ethylphosphocholine (EDOPC), 1-palmitoyl-2-oleoyl-sn-glycero-3-ethylphosphocholine (EPOPC), 1,2-dimyristoyl-sn-glycero-3-ethylphosphocholine (EDMPC), 1,2-distearoyl-sn-glycero-3-ethylphosphocholine (SPC), 1,2-dipalmitoyl-sn-glycero-3-ethylphosphocholine (EDPPC), 1,2-dioleoyl-3-trimethylammonium-propane (DOTAP), N-[1-(2,3-dioleyloxy)propyl]-N,N,N-trimethylammonium chloride (DOTMA) and 3β-[N-(N',N'-dimethylaminoethane)-carbamoyl]cholesterol (DC-Cholesterol).

Further, the cationic liposome may further include, but are not limited to, at least one auxiliary lipid selected from the group consisting of 1,2-diacyl-sn-glycero-3-phosphoethanolamine (DOPE), 1,2-diphytanoyl-sn-glycero-3-phosphoethanolamine (DPhPE), 1,2-dioleoyl-sn-glycero-3-phosphocholine (DOPC), 1,2-dioleoyl-sn-glycero-3-[phospho-L-serine] (DOPS), 1,2-dioleoyl-sn-glycero-3-ethylphosphocholine (DO-Ethyl-PC), and cholesterol.

In one embodiment of the present invention, the nucleic acid delivery system may be a cationic polymer.

Examples of the cationic polymer may include, but are not limited to, at least one polymer selected from the group consisting of poly-L-lysine, poly-L-ornithine, poly-L-histidine, poly-L-arginine, bis(3-aminopropyl)terminated polytetrahydrofuran, polyacrylamide (PA), poly(α-[4-aminobutyl]-L-glycolic acid (PAGA), poly(2-aminoethyl propylene phosphate) (PPE-EA), cationic derivatives of cyclodextrin, poly(2-(dimethylamino)ethyl methacrylate (pDMAEMA), poly(4-vinylpyridine) (P4VP), O,O'-bis(2-aminopropyl) polypropylene glycol-block-polyethylene glycol-block-polypropylene glycol, chitosan, chitosan derivatives, polyethylenimine (PEI), polyethylenimine derivatives, polyamidoamine (PAMAM), fractured PAMAM and poly-N-ethyl-4-vinylpyridinium tribromide.

The nucleic acid delivery system of the present invention in the form of a cationic liposome or cationic polymer formulation is positively charged. Therefore, due to the presence of positive charges of the nucleic acid delivery system and negative charges of the nucleic acid, a complex between the nucleic acid delivery system and the nucleic acid may be formed via electrostatic bonding, even when they are simply mixed.

Further, the pharmaceutical composition for treating cancer in accordance with the present invention may achieve synergistic therapeutic effects by further incorporation of conventionally known cancer chemotherapeutic agents, in addition to the siRNA component that inhibits the expression of Wnt1. Examples of the cancer chemotherapeutic agent that may be administered in combination with the Wnt1 expression-inhibiting siRNA of the present invention may include cisplatin, carboplatin, oxaliplatin, doxorubicin, daunorubicin, epirubicin, idarubicin, mitoxantrone, valrubicin, curcumin, gefitinib, erlotinib, irinotecan, topotecan, vinblastine, vincristine, docetaxel, and paclitaxel.

The composition of the present invention may further comprise pharmaceutically acceptable carrier(s), in addition to siRNA or a complex of siRNA with the nucleic acid delivery system. Examples of suitable pharmaceutically acceptable carriers may include water, saline, PBS (phosphate buffered saline), dextrin, glycerol, and ethanol. These materials may be used alone or in any combination thereof. Additionally, the composition of the present invention may be appropriately formulated into a desired dosage form by a conventional method known in the art, such that it is possible to achieve fast, sustained or delayed release of active ingredients after administration of the composition to a subject in need thereof.

The siRNA or siRNA/nucleic acid delivery system complex of the present invention may be introduced into target cells for treatment of cancer. As can be confirmed through the following Examples, intracellular introduction of the siRNA or siRNA/nucleic acid delivery system complex results in inhibition of expression of Wnt1 involved in carcinogenesis, which leads to death of cancer cells.

Further, the present invention provides a use of siRNA that inhibits intracellular expression of Wnt1 through complementary binding to a Wnt1 transcript (mRNA transcript) base sequence as set forth in SEQ ID NO: 2, SEQ ID NO: 7 or SEQ ID NO: 14, for the preparation of an anticancer drug. Further, the present invention provides a method for treating cancer comprising introducing to cells of a subject a therapeutically effective amount of siRNA that inhibits intracellular expression of Wnt1 through complementary binding to a Wnt1 transcript (mRNA transcript) base sequence as set forth in SEQ ID NO: 2, SEQ ID NO: 7 or SEQ ID NO: 14. In the present invention, cancer treatment includes prevention and inhibition of cancer. The subject of the present invention includes mammals such as humans, and the like.

Further, the present invention provides a use of an siRNA/nucleic acid delivery system complex that inhibits intracellular expression of Wnt1 through complementary binding to a Wnt1 transcript (mRNA transcript) base sequence as set forth in SEQ ID NO: 2, SEQ ID NO: 7 or SEQ ID NO: 14, for the preparation of an anticancer drug. Further, the present invention provides a method for treating cancer comprising introducing to cells of a subject a therapeutically effective amount of an siRNA/nucleic acid delivery system complex that inhibits intracellular expression of Wnt1 through complementary binding to a Wnt1 transcript (mRNA transcript) base sequence as set forth in SEQ ID NO: 2, SEQ ID NO: 7 or SEQ ID NO: 14.

In vivo or ex vivo intracellular introduction of a desired nucleic acid by means of the pharmaceutical composition of the present invention results in a selective reduction of expression of the target protein Wnt1 or otherwise correction of mutations of the target gene, which makes it possible to treat cancer caused by overexpression of Wnt1.

Further, the present invention provides a method for treating cancer comprising introducing to cells of a subject a therapeutically effective amount of the pharmaceutical composition of the present invention.

As used herein, the term "therapeutically effective amount" refers to an amount of the siRNA or siRNA/nucleic acid delivery system complex that is required to exert anticancer effects. As will be apparent to those skilled in the art, the effective dose of the active drug ingredient may vary depending upon various factors such as kinds of diseases, severity of diseases, kinds of nucleic acids to be administered, kinds of dosage forms, age, weight, general health status, sex and dietary habits of patients, administration times and routes, treatment duration, and drugs such as co-administered chemical anticancer drugs. For adults, the anticancer composition may be preferably administered at a dose of 0.001 mg/kg to 100 mg/kg once a day.

In the following Examples, a candidate sequence group suited for the construction of siRNAs effective for inhibition of Wnt1 expression was selected from among the full-length transcript sequence of Wnt1, the corresponding siRNAs were synthesized and treated on tumor cell lines using a delivery system (such as liposome, cationic polymer, etc), and RNA-mediated expression interference was then confirmed at the transcript level by reverse transcription-polymerase chain reaction (RT-PCR). In order to evaluate effects of inhibition of Wnt1 expression on growth of tumor cells, tetrazolium 3-(4,5-dimethylthiazol-2-yl)-2,5-diphenyl tetrazolium bromide (MTT) staining, lactate dehydrogenase (LDH) assay, Annexin V-FITC (fluorescein isothiocyanate)/PI(propidium iodide) staining and cell staining were carried out on the cell groups which were treated with siRNAs for Wnt1.

According to the results of the following Examples, among siRNAs of the present invention that inhibit intracellular expression of Wnt1 through complementary binding to a Wnt1 transcript (mRNA transcript) base sequence as set forth in SEQ ID NO: 2, SEQ ID NO: 7 or SEQ ID NO: 14, it was confirmed that siRNA having a sense sequence of SEQ ID NO: 18 and an antisense sequence of SEQ ID NO: 19, siRNA having a sense sequence of SEQ ID NO: 28 and an antisense sequence of SEQ ID NO: 29, and siRNA having a sense sequence of SEQ ID NO: 42 and an antisense sequence of SEQ ID NO: 43 are particularly effective for the inhibition of Wnt1 expression. Therefore, the present invention provides siRNA having a sense sequence of SEQ ID NO: 18 and an antisense sequence of SEQ ID NO: 19, siRNA having a sense sequence of SEQ ID NO: 28 and an antisense sequence of SEQ ID NO: 29, and siRNA having a sense sequence of SEQ ID NO: 42 and an antisense sequence of SEQ ID NO: 43, and pharmaceutical compositions for treating cancer comprising the same. Further, the present invention provides a method for treating cancer comprising introducing to cells of a subject a therapeutically effective amount of at least one siRNA selected from the group consisting of siRNA having a sense sequence of SEQ ID NO: 18 and an antisense sequence of SEQ ID NO: 19, siRNA having a sense sequence of SEQ ID NO: 28 and an antisense sequence of SEQ ID NO: 29, and siRNA having a sense sequence of SEQ ID NO: 42 and an antisense sequence of SEQ ID NO: 43.

Advantageous Effects siRNA of the present invention which is complementary to a base sequence of a Wnt1 transcript (mRNA) provides apoptotic cancer cell death due to inhibition of expression of Wnt1 commonly expressed in cancer cells, by RNA-mediated interference (RNAi). Therefore, the composition of the present invention comprising the same can be used as an excellent anticancer drug.

MODE FOR INVENTION

Figure 1:
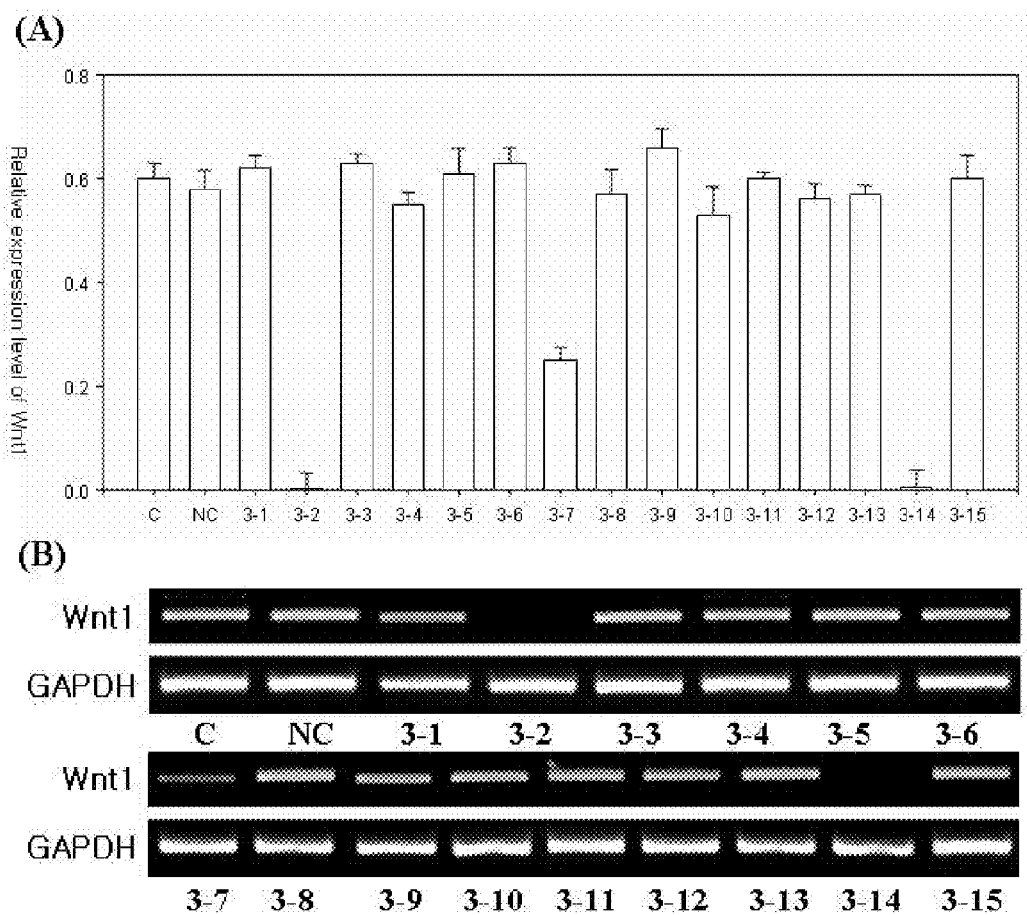
FIG. 1 shows the RT-PCR assay results confirming Wnt1 expression-inhibiting siRNA-mediated inhibitory effects on Wnt1 transcript expression in the human hepatoma cell line Hep3B.

The present invention will be described in more detail with reference to the following Examples.

These and other objects, advantages and features of the present invention will become apparent from the detailed embodiments given below which are made in conjunction with the following Examples. The present invention may be embodied in different forms and should not be misconstrued as being limited to the embodiments set forth herein, and those skilled in the art will appreciate that various modifications, additions and substitutions are possible without departing from the scope and spirit of the invention as disclosed in the accompanying claims. Therefore, it should be understood that the embodiments disclosed herein are provided only for illustrating the present invention and should not be construed as limiting the scope and spirit of the present invention.

EXAMPLE 1

Design of Target Base Sequence Candidate Group to Which Wnt1 Expression-inhibiting siRNAs can Bind A target base sequence candidate group where siRNAs can bind in a transcript of Wnt1 was designed.

Using an appropriate siRNA design program for a desired base sequence, target base sequences where siRNAs can bind in the Wnt1 mRNA sequence (NM_005430) were first designed.

Table 1 below sets forth sources for siRNA design programs and Table 2 below provides a candidate group of target base sequences of in silico-designed siRNAs which were finally selected in the present invention using programs of Table 1.

TABLE 1 siRNA design programs

| Design program name | Source |
| --- | --- |
| siRNA Sequence Designer (Clontech) | Available at the Clontech Laboratories (Mountain View, CA, USA) website. |
| GenScript siRNA Target Finder | Available at the GenScript USA Inc. (Piscataway, NJ, USA) website. |
| siRNA Design Tool (Qiagen) | Available at the Qiagen, Inc. (Valencia, CA, USA) website. |
| Find siRNA sequences (Invivogen) | Available at the InvivoGen (San Diego, CA, USA) website. |
| siRNA Selection Program (WI) | Available at the Whitehead Institute for Biomedical Research (Cambridge, MA, USA) website. |
| siRNA Target Finder (Ambion) | Available at the Ambion (Applied Biosystems/ Ambion, Austin, TX, USA) website. |

TABLE 2

Target base sequence candidate group where siRNAs can bind in Wnt1 mRNA (NM_005430)

| SEQ ID NO: | Base start No. | Base sequence |
| --- | --- | --- |
| 1 | 326 | CCACGAACCUGCUUACAGA |
| 2 | 333 | CCUGCUUACAGACUCCAAG |
| 3 | 396 | CAAACAGCGGCGUCUGAUA |
| 4 | 550 | AACCGAGGCUGUCGAGAAA |
| 5 | 559 | UGUCGAGAAACGGCGUUUA |
| 6 | 561 | UCGAGAAACGGCGUUUAUC |
| 7 | 567 | CGGCGUUUAUCUUCGCUAU |
| 8 | 627 | UCAGAAGGUUCCAUCGAAU |
| 9 | 653 | CGUGUGACUACCGGCGGCG |
| 10 | 707 | CAGCGACAACAUUGACUUC |
| 11 | 785 | UCCUCAUGAACCUUCACAA |
| 12 | 817 | GUACGACCGUAUUCUCCAA |
| 13 | 1075 | GAGAAAUCGCCCAACUUCU |

TABLE 2-continued

Target base sequence candidate group where siRNAs can bind in Wnt1 mRNA (NM_005430)

| SEQ ID NO: | Base start No. | Base sequence |
|---|---|---|
| 14 | 1079 | AUCGCCCAACUUCUGCACG |
| 15 | 1273 | AACUGCACGCACGCGCGUA |

EXAMPLE 2

Construction of siRNA Candidate Group for Inhibition of Wnt1 Expression 15 siRNAs capable of binding to the target base sequences designed in Example 1 were synthesized using a Silencer™ siRNA Construction Kit (Ambion Inc., Texas, USA) according to the manufacturer's instruction. Sequences of 15 siRNA candidates as thus synthesized are given in Table 3 below.

TABLE 3

Base sequence candidate group of Wnt1 expression-inhibiting siRNAs

| Example No. | SEQ ID NO | Sense base sequence (5'-3')<br>Antisense base sequence (5'-3') | Base start No. |
|---|---|---|---|
| 2-1 | 16<br>17 | CCACGAACCUGCUUACAGAUU<br>UCUGUAAGCAGGUUCGUGGUU | 326 |
| 2-2 | 18<br>19 | CCUGCUUACAGACUCCAAGUU<br>CUUGGAGUCUGUAAGCAGGUU | 333 |
| 2-3 | 20<br>21 | CAAACAGCGGCGUCUGAUAUU<br>UAUCAGACGCCGCUGUUUGUU | 396 |
| 2-4 | 22<br>23 | AACCGAGGCUGUCGAGAAAUU<br>UUUCUCGACAGCCUCGGUUU | 550 |
| 2-5 | 24<br>25 | UGUCGAGAAACGGCGUUUAUU<br>UAAACGCCGUUUCUCGACAUU | 559 |
| 2-6 | 26<br>27 | UCGAGAAACGGCGUUUAUCUU<br>GAUAAACGCCGUUUCUCGAUU | 561 |
| 2-7 | 28<br>29 | CGGCGUUUAUCUUCGCUAUUU<br>AUAGCGAAGAUAAACGCCGUU | 567 |
| 2-8 | 30<br>31 | UCAGAAGGUUCCAUCGAAUUU<br>AUUCGAUGGAACCUUCUGAUU | 627 |
| 2-9 | 32<br>33 | CGUGUGACUACCGGCGGCGUU<br>CGCCGCCGGUAGUCACACGUU | 653 |
| 2-10 | 34<br>35 | CAGCGACAACAUUGACUUCUU<br>GAAGUCAAUGUUGUCGCUGUU | 707 |
| 2-11 | 36<br>37 | UCCUCAUGAACCUUCACAAUU<br>UUGUGAAGGUUCAUGAGGAUU | 785 |
| 2-12 | 38<br>39 | GUACGACCGUAUUCUCCAAUU<br>UUGGAGAAUACGGUCGUAGUU | 817 |
| 2-13 | 40<br>41 | GAGAAAUCGCCCAACUUCUUU<br>AGAAGUUGGGCGAUUUCUCUU | 1075 |
| 2-14 | 42<br>43 | AUCGCCCAACUUCUGCACGUU<br>CGUGCAGAAGUUGGGCGAUUU | 1079 |
| 2-15 | 44<br>45 | AACUGCACGCACGCGCGUAUU<br>UACGCGCGUGCGUGCAGUUUU | 1273 |

EXAMPLE 3

Preparation of Wnt1 Expression-inhibiting siRNA/Cationic Liposome Complexes

Complexes of 15 Wnt1 expression-inhibiting siRNAs synthesized in Example 2 with a cationic liposome for carrying them were prepared.

First, cell-fusogenic phospholipid 1,2-diacyl-sn-glycero-3-phosphoethanolamine (DOPE), cholesterol, and cationic phospholipid 1,2-dioleoyl-sn-glycero-3-ethylphosphocholine (EDOPC) (Avanti Polar Lipids Inc., USA) were taken in a molar ratio of 1:1:1, mixed in a glass vial, and then rotary-evaporated at a low speed under a nitrogen atmosphere, thereby preparing a lipid thin film. For preparation of lipid multilamellar vesicles (MLVs), 1 mL of a phosphate-buffered solution (PBS) was added to the thus-prepared thin film, and the vial was then sealed, followed by vortexing for 3 min at 37° C. To obtain a uniform particle size, the film solution was passed three times through a 0.2 μm polycarbonate membrane using an extruder (Northern Lipids Inc., Canada). The resulting cationic liposome was mixed with each of 15 Wnt1 expression-inhibiting siRNAs of Example 2, and the mixtures were allowed to stand at room temperature for 20 min to prepare siRNA/cationic liposome complexes. The compositions of the siRNA/cationic liposome complexes prepared in Example 3 are summarized in Table 4 below.

TABLE 4

Compositions of the siRNA/cationic liposome complexes

| Example No. | Wnt1 siRNA | Cationic liposome |
|---|---|---|
| 3-1 | Example 2-1 | DOPE + Cholesterol + EDOPC |
| 3-2 | Example 2-2 | |
| 3-3 | Example 2-3 | |
| 3-4 | Example 2-4 | |
| 3-5 | Example 2-5 | |
| 3-6 | Example 2-6 | |
| 3-7 | Example 2-7 | |
| 3-8 | Example 2-8 | |
| 3-9 | Example 2-9 | |
| 3-10 | Example 2-10 | |
| 3-11 | Example 2-11 | |
| 3-12 | Example 2-12 | |
| 3-13 | Example 2-13 | |
| 3-14 | Example 2-14 | |
| 3-15 | Example 2-15 | |

EXAMPLE 4

Preparation of Wnt1 Expression-inhibiting siRNA/Cationic Polymer Complexes

Each binary set of Wnt1 expression-inhibiting siRNAs synthesized in Example 2 was mixed with a cationic polymer polyethylenimine (PEI) to prepare three complexes. PEI 25 kD (Sigma-Aldrich, USA) was dissolved in water, adjusted to a molar concentration of 1 mM, placed in a 100 mL Pyrex glass round-bottom flask, and adjusted to pH 5 with addition of 1N hydrochloric acid. Then, the solution was passed through a 0.2 μm pore-size syringe filter membrane to remove impurities to thereby prepare a cationic polymer. Among Wnt1 expression-inhibiting siRNAs synthesized in Example 2, siRNAs were selected as binary combinations set forth in Table 5 below. The above prepared cationic polymer was mixed with each of the selected siRNA sets, and the mixtures were allowed to stand at room temperature for 20 min to prepare complexes.

TABLE 5

Composition of the siRNA/cationic polymer complexes

| Example No. | Wnt1 siRNA | Cationic polymer |
|---|---|---|
| 4-1 | Example 2-2 + Example 2-7 | Polyethylenimine |
| 4-2 | Example 2-2 + Example 2-14 | |
| 4-3 | Example 2-7 + Example 2-14 | |

Comparative Example 1

Preparation of Luciferase GL2 Expression-inhibiting siRNA/Cationic Liposome Complexes As a negative control for comparison of cytotoxicity of siRNA per se, a conventional commercially-available product, luciferase GL2 expression-inhibiting siRNA was purchased from Samchully Pharm. Co., Ltd. (Seoul, Korea). A base sequence of the luciferase GL2 expression-inhibiting siRNA has SEQ ID NO: 46 (5'-CGUACGCGGAAUACU-UCGATT-3')(forward) and SEQ ID NO: 47 (5'-UC-GAAGUAUUCCGCGUACGTT-3') (reverse). The luciferase GL2 expression-inhibiting siRNA was mixed with the cationic liposome prepared in Example 3, and the mixture was allowed to stand at room temperature for 20 min to thereby prepare a complex composition of siRNA and cationic liposome.

Culture of Hepatoma Cell Line Hep3B

The hepatoma cell line Hep3B cell line was purchased from American Type Culture Collection (ATCC, USA). The Hep3B cell line was cultured in Dulbecco's Modified Eagles Medium (DMEM, Gibco, USA) containing 10% w/v fetal bovine serum (FBS, HyClone Laboratories Inc., USA) and 100 units/mL of penicillin or 100 μg/mL of streptomycin.

EXAMPLE 5

RT-PCR Assay for Inhibitory Effects of Wnt1 Expression-inhibiting siRNAs on Expression of Wnt1 Transcript In order to evaluate apoptotic effects of Wnt1-targeted siRNA-containing compositions on cancer cells, experiments were carried out according to the following procedure using reverse transcription-polymerase chain reaction (RT-PCR).

On the day prior to the experiment, 8×10$^4$ cells/well of the Hep3B cell line were seeded on 24-well plates. When cells of each plate were grown to 50% to 70% confluence, the culture media were replaced with 250 μl/well of fresh media.

50 μl of serum-free medium was added to Eppendorf tubes to which the complex composition of the luciferase GL2 expression-inhibiting siRNA with the cationic liposome (Comparative Example 1) and the complex compositions of 15 Wnt1 expression-inhibiting siRNAs with the cationic liposome (Examples 3-1 to 3-15) were then added, respectively. A final concentration of siRNA in the media was adjusted to 50 nM. These materials were slowly pipetted, mixed and allowed to stand at room temperature for 20 min, thus resulting in formation of a composition. The thus-prepared composition was added to the well plate, followed by cell culture in a $CO_2$ incubator at 37° C. for 24 hours.

After 24 hours, total RNA was isolated from cultured cells using Trizol reagent (Invitrogen, Carlsbad, Calif., USA) and then reverse-transcribed into cDNA using AccuPower RT PreMix (Bioneer, Daejeon, Korea). The Wnt1-specific primer used for PCR had a sequence of SEQ ID NO: 48 (5'-CG-GCGTTTATCTTCGCTATC-3') (left) and SEQ ID NO: 49 (5'-GCCTCGTTGTTGTGAAGGTT-3') (right), and the size of the PCR product was 244 bp in length. Expression of the Wnt1 transcript (mRNA transcript) was assayed by determining quantitative changes of the gene expression through normalization of a band density of the Wnt1-specific PCR product against a band density obtained by amplification of a GAPDH (glyceraldehyde-3-phosphate dehydrogenase) transcript.

FIG. 1 shows the RT-PCR assay results confirming Wnt1 expression-inhibiting siRNA-mediated inhibitory effects on Wnt1 transcript expression in the human hepatoma cell line Hep3B. A: Numerical representation of relative expression of Wnt1 transcript, and B: Representative electrophoretic pattern showing expression levels of Wnt1 transcript. In FIG. 1, "C" represents a control group, "NC" represents a group treated with the complex composition of Comparative Example 1, and 3-1 to 3-15 represent groups treated with complex compositions of Examples 3-1 through 3-15. The control group (C) was a non-treated group where expression of the Wnt1 transcript was observed; the Comparative Example 1-treated group (NC) was a luciferase GL2 RNA-treated group where there was no significant change in expression of the Wnt1 transcript, as compared to the control group; and Example 3-1 to 3-15-treated groups exhibited various expression inhibitory effects when compared with the control group. Particularly the groups treated with the complexes of Examples 3-2, 3-7 and 3-14 exhibited a significant decrease in expression of the Wnt1 transcript. Therefore, it can be seen from FIG. 1 that siRNAs prepared in Examples 2-2, 2-7 and 2-14 were delivered intracellularly to the Hep3B cell line to thereby result in selective inhibition of the Wnt1 expression.

EXAMPLE 6

MTT Assay for Antitumor Effects of Wnt1 Expression-inhibiting siRNAs

In order to evaluate apoptotic effects of Wnt1-targeted siRNA-containing compositions on cancer cells, experiments were carried out according to the following procedure using the MTT (3-(4,5-dimethylthiazol-2-yl)-2,5-diphenyl tetrazolium bromide)colorimetric assay.

On the day prior to the experiment, 8×04 cells/well of the Hep3B cell line were seeded on 24-well plates. When cells of each plate were grown to 50% to 70% confluence, the culture media of the plates were replaced with 250 μl/well of fresh serum-free media.

50 μl of serum-free medium was added to Eppendorf tubes to which the complex composition of the luciferase GL2 expression-inhibiting siRNA with the cationic liposome (Comparative Example 1) and the complex compositions of 15 Wnt1 expression-inhibiting siRNAs with the cationic liposome (Examples 3-1 to 3-15) were then added, respectively. A final concentration of siRNA in the media was adjusted to 50 nM. These materials were slowly pipetted, mixed and allowed to stand at room temperature for 20 min, thus resulting in formation of a composition. The thus-prepared complex composition was added to the well plate, followed by cell culture in a $CO_2$ incubator at 37° C. for 24 hours.

48 hours after treatment of the cells with individual complex compositions, an MTT solution was added to make 10% of the medium, followed by cell culture for another 4 hours. The supernatant was discarded and a 0.06 N isopropanol hydrochloride solution was added to the medium. The absorbance was then measured at 570 nm using an ELISA reader. Non-treated cells were used as a control group.

Figure 2:
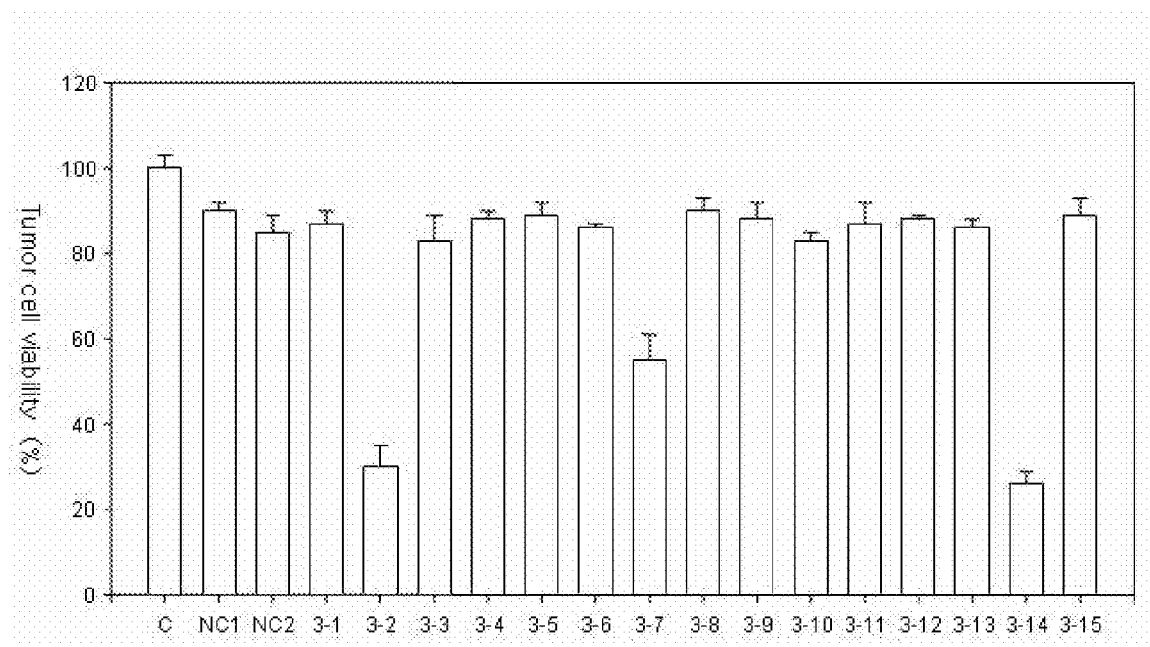
FIG. 2 shows the MTT staining assay results confirming Wnt1 expression-inhibiting siRNA-mediated apoptotic effects on cancer cells in the human hepatoma cell line Hep3B.

FIG. 2 shows the results confirming Wnt1 expression-inhibiting siRNA-mediated cancer cell apoptosis in the human hepatoma cell line Hep3B, using the MTT staining method. In FIG. 2, "C" represents a control group, "NC1" represents a (nucleic acid delivery system) cationic liposome-alone treated group, "NC2" represents a group treated with the complex of Comparative Example 1, and 3-1 to 3-15 represent groups treated with siRNA/cationic liposome complex compositions of Examples 3-1 through 3-15. The control group (C) was a non-treated group where the tumor cell viability should be 100%; the delivery system liposome-alone treated group "NC1" exhibited no significant changes in the cell viability due to no incorporation of siRNA, as compared to the control group; Comparative Example 1-treated group "NC2" was a group treated with luciferase GL2-inhibiting siRNA which exhibited substantially no effects on the viability of tumor cells; and particularly the groups treated with complex compositions of Examples 3-2, 3-7 and 3-14 exhibited a pronounced decrease in the viability of tumor cells, when the groups treated with siRNA/cationic liposome complex compositions of Examples 3-1 through 3-15 were compared with the control group. Therefore, it can be seen from FIG. 2 that siRNAs prepared in Examples 2-2, 2-7 and 2-14 were delivered intracellularly to the Hep3B cell line to thereby result in selective suppression of the Wnt1 expression, thus exerting antitumor effects.

EXAMPLE 7

LDH Assay for Antitumor Effects of Wnt1 Expression-inhibiting siRNAs

In order to examine damage effects of Wnt1 expression-inhibiting siRNA-containing compositions on tumor cells, experiments were carried out according to the following procedure using an LDH Cytotoxicity Detection kit (TAKARA Bio Inc., Otsu Shiga, Japan) that detects with high sensitivity lactate dehydrogenase (LDH) extracellularly secreted due to damage of the tumor cells.

On the day prior to the experiment, $8 \times 10^4$ cells/well of the Hep3B cell line were seeded on 24-well plates. When cells of each plate were grown to 50% to 70% confluence, the culture media were replaced with 250 μl/well of fresh serum-free media.

50 μl of serum-free medium was added to Eppendorf tubes to which the complex composition of the luciferase GL2 expression-inhibiting siRNA with the cationic liposome (Comparative Example 1) and the complex compositions of 15 Wnt1 expression-inhibiting siRNAs with the cationic liposome (Examples 3-1 to 3-15) were then added, respectively. A final concentration of siRNA in the media was adjusted to 50 nM. These materials were slowly pipetted, mixed and allowed to stand at room temperature for 20 min, thus resulting in formation of a complex. The thus-prepared complex was added to the well plate, followed by cell culture in a $CO_2$ incubator at 37° C. for 24 hours. At this time, Triton X-100 was added at a concentration of 3% to the plate such that a maximum LDH activity could be measured, followed by cell culture in a $CO_2$ incubator at 37° C. 48 hours after treatment of the cells with individual complexes, the tissue culture plate was centrifuged at 250×g for 10 min and 100 μl/well of the supernatant was transferred to another clear 96-well plate. The reaction mixture was prepared according to the manufacturer's protocol, followed by addition of 100 μl/well. The plate was shielded from light and allowed to stand at room temperature for 30 min. The absorbance was measured at 492 nm using an ELISA reader. A blank medium was used as a negative control, and cells with treatment of 3% Triton X-100 were used as a positive control. % damage of tumor cells was calculated according to the following equation:

% damage of tumor cells=[(absorbance of experimental group−absorbance of negative control group)/(absorbance of positive control group−absorbance of negative control group)×100]

Figure 3:
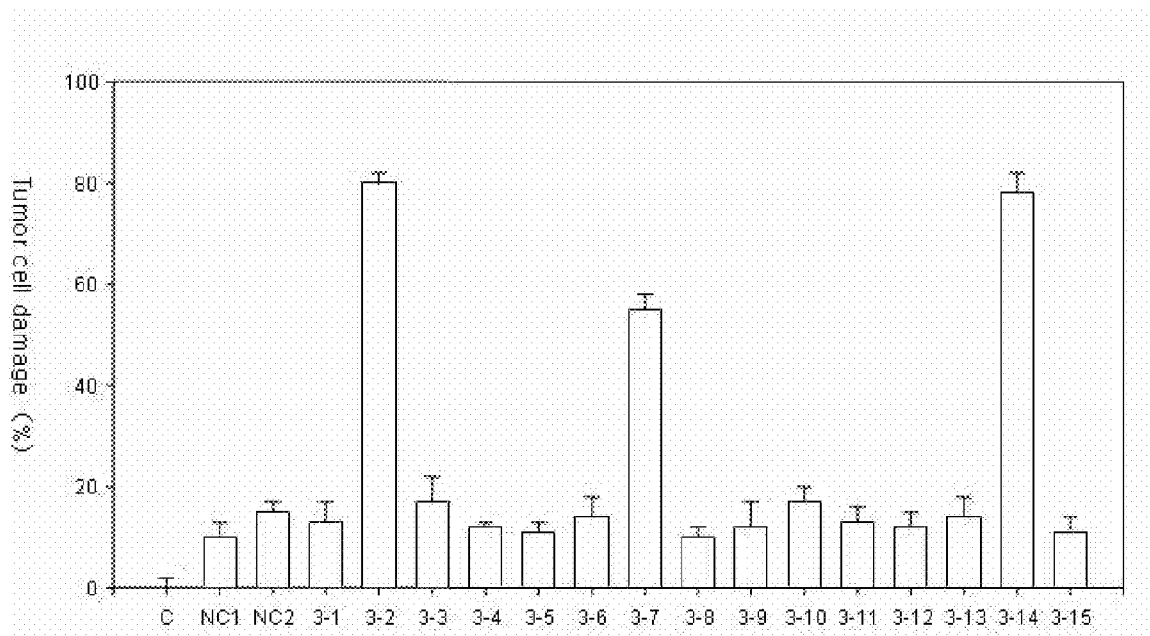
FIG. 3 shows the LDH assay results confirming apoptotic effects of Wnt1 expression-inhibiting siRNA in the human hepatoma cell line Hep3B.

FIG. 3 shows the LDH assay results confirming apoptotic effects of Wnt1 expression-inhibiting siRNA in the human hepatoma cell line Hep3B. In FIG. 3, "C" represents a control group, "NC1" represents a (nucleic acid delivery system) cationic liposome-alone treated group, "NC2" represents a group treated with the complex composition of Comparative Example 1, and 3-1 to 3-15 represent groups treated with the complex compositions of Examples 3-1 through 3-15. The control group (C) was a non-treated group where there were no noticeable changes in the tumor cell damage (%); the cationic liposome-alone treated group "NC1" exhibited no significant changes in the tumor cell damage (%) due to no incorporation of siRNA, as compared to the control group; Comparative Example 1-treated group "NC2" exhibited no significant changes in the tumor cell damage (%) due to the absence of RNA-mediated interference of the luciferase GL2-inhibiting siRNA; and particularly the groups treated with siRNA/cationic liposome complex compositions of Examples 3-2, 3-7 and 3-14 exhibited a pronounced increase in the tumor cell damage (%), when the groups treated with the complex compositions of Examples 3-1 through 3-15 were compared with the control group. Therefore, it can be seen from FIG. 3 that siRNAs prepared in Examples 2-2, 2-7 and 2-14 were delivered intracellularly to the Hep3B cell line to thereby result in selective suppression of the Wnt1 expression, thus exerting antitumor effects.

EXAMPLE 8

FACS Assay for Apoptotic Effects of Wnt1 Expression-inhibiting siRNAs on Cancer Cells In order to evaluate apoptotic effects of Wnt1 expression-inhibiting siRNA-containing compositions on cancer cells, experiments were carried out according to the following procedure using the Fluorescence Activated Cell Sorting (FACS) assay.

The hepatoma cell line (Hep3B) was treated with the complex composition of luciferase GL2 expression-inhibiting siRNA and a cationic liposome (Comparative Example 1), the complex compositions of Wnt1 expression-inhibiting siRNA and a cationic liposome (Examples 3-7, 3-11 and 3-14), and the complex compositions of two Wnt1 expression-inhibiting siRNAs and a cationic polymer polyethylenimine (Examples 4-1 and 4-3), respectively, followed by evaluation of apoptotic cell death. The cell death evaluation was carried out using an Annexin V-FITC Apoptosis Detection kit (BD Biosciences, USA).

On the day prior to the experiment, $2 \times 10^5$ cells/well of the Hep3B cell line were seeded on 6-well plates. When cells of each plate were grown to 40% to 50% confluence, the culture media of the plates were replaced with 1400 μl/well of fresh serum-free media.

50 μl of serum-free medium was added to Eppendorf tubes to which the complex composition of the luciferase GL2 expression-inhibiting siRNA with a liposome (Comparative Example 1), the complex compositions of Wnt1 expression-inhibiting siRNA with the liposome (Examples 3-7, 3-11 and 3-14), and the complex compositions of two Wnt1 expression-inhibiting siRNAs with a cationic polymer polyethylenimine (Examples 4-1 and 4-3) were then added, respectively. A final concentration of siRNA in the media was adjusted to 50 nM. These materials were slowly pipetted, mixed and allowed to stand at room temperature for 20 min, thus resulting in formation of a complex composition. The thus-prepared complex composition was added to the well plate, followed by cell culture in a $CO_2$ incubator at 37C. 92 hours after treatment of the cells with individual complex compositions, the cultured cells were collected and washed two times with PBS, followed by staining for 30 min under light shielding conditions, using annexin V-FITC and propidium iodide (PI). Then, the apoptotic efficiency of the complex was analyzed by means of a shift of fluorescence intensity peak using a BD FACSCalibur flow cytometry system (BD Biosciences, USA). The shift of fluorescence intensity peak was normalized using a non-RNA treated cell group and the annexin V-FITC/PI-alone treated and stained cell group, respectively.

Figure 4:
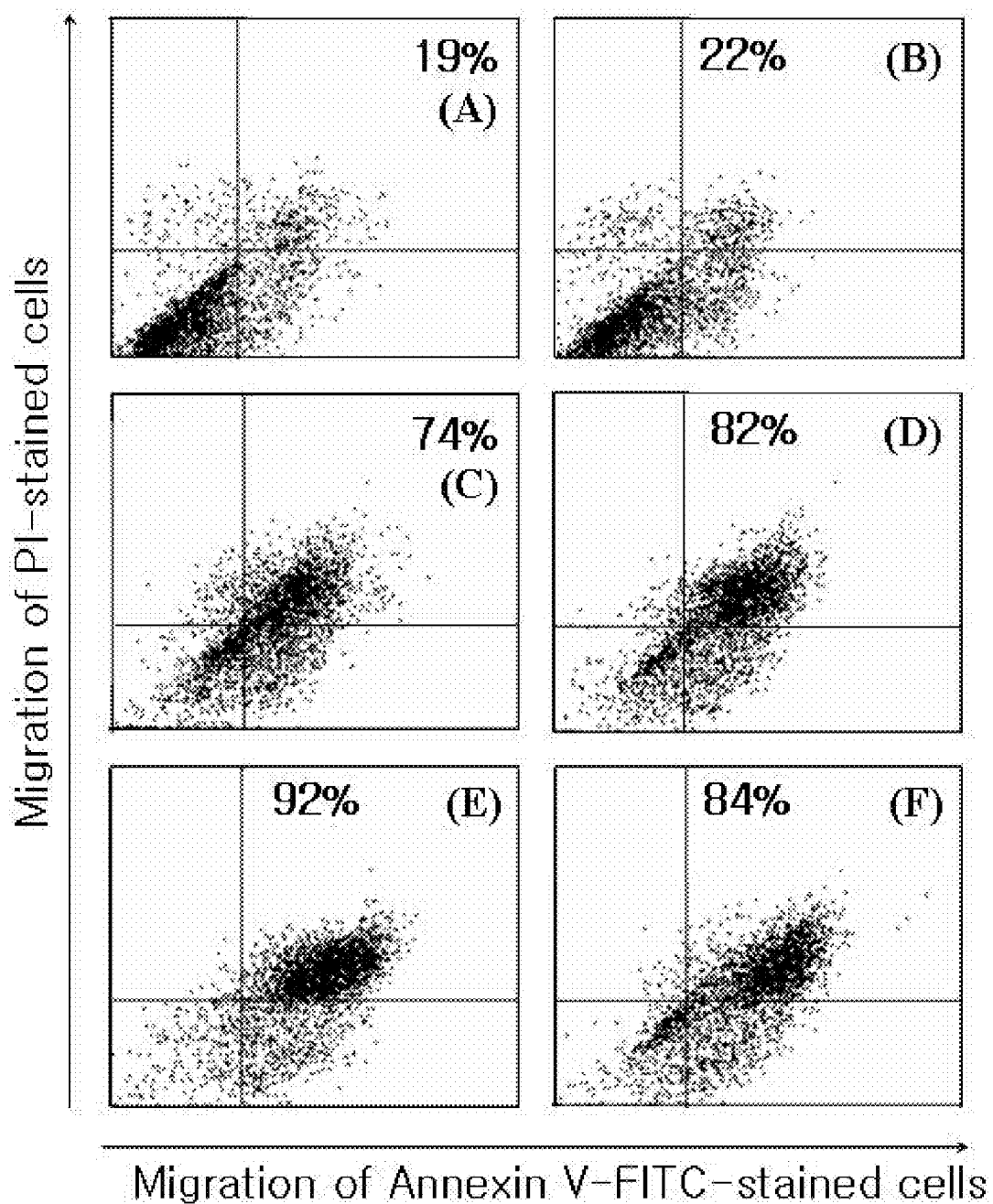
FIG. 4 shows the annexin V-FITC/PI staining assay results confirming apoptotic effects of Wnt1 expression-inhibiting siRNA in the human hepatoma cell line Hep3B.

FIG. 4 shows the assay results confirming apoptotic effects of Wnt1 expression-inhibiting siRNA in the human hepatoma cell line Hep3B, using the annexin V-FITC/PI staining method. The cells were treated as follows. A: Complex of Comparative Example 1, B: Complex composition of Example 3-11 having no Wnt1 transcript expression-inhibitory activity, C: Complex composition of Example 3-7, D: Complex composition of Example 3-14, E: Complex composition of Example 4-1, and F: Complex composition of Example 4-3. The group treated with the complex composition of Comparative Example 1 exhibited 19% in a fraction of annexin V-positive cells, that is apoptosis-committed cells (FIG. 4A); Example 5 exhibited no inhibitory effects on the Wnt1 transcript; and Examples 6 and 7, where the cell groups were treated with the complex composition of Example 3-11 having no antitumor activity, exhibited 22% in a fraction of annexin V-positive cells, which is similar to the level of Comparative Example 1-treated group (FIG. 4B). On the other hand, each siRNA composition of Examples 3-7 and 3-14 exhibited 74% and 82% in the fraction of annexin V-positive cells, thus representing that the fraction of cells induced to undergo apoptosis was significantly increased (FIGS. 4C and 4D). The cell groups treated with the complex composition containing two Wnt1 expression-inhibiting siRNAs, e.g. the complex composition of Example 4-1 (siRNA of Example 2-2+siRNA of Example 2-7) and the complex composition of Example 4-3 (siRNA of Example 2-7+siRNA of Example 2-14), exhibited 92% and 84% in the fraction of annexin V-positive cells induced to undergo apoptosis (FIGS. 4E and 4F). Therefore, it can be seen through FIG. 4 that siRNA compositions prepared in Examples 3-7 and 3-14 exhibited selective suppression of the Wnt1 expression, thereby providing antitumor effects. Further, as observed in the groups treated with the complex compositions of Examples 4-1 and 4-3, combined use of two effective siRNAs can also exhibit antitumor effects.

EXAMPLE 9

Assay for Apoptotic Effects of Wnt1 siRNAs on Cancer Cells (Via Residual Cell Staining Method)

In order to evaluate apoptotic effects of Wnt1 siRNA-containing compositions on cancer cells, experiments were carried out according to the following procedure using the residual cell staining method.

The hepatoma cell line (Hep3B) was treated with the complex composition of luciferase GL2 expression-inhibiting siRNA and a cationic liposome (Comparative Example 1), the complex compositions of Wnt1 expression-inhibiting siRNA and a cationic liposome (Examples 3-2, 3-5 and 3-7), and the complex compositions of two Wnt1 expression-inhibiting siRNAs and a cationic polymer polyethylenimine (Example 4-2), respectively, followed by evaluation of apoptotic cell death. The cell death evaluation was carried out by a cell staining method using a crystal violet dye.

On the day prior to the experiment, $2\times10^5$ cells/well of the Hep3B cell line were seeded on 6-well plates. When cells of each plate were grown to 40% to 50% confluence, the culture media of the plates were replaced with 1400 µl/well of fresh serum-free media.

50 µl of serum-free medium was added to Eppendorf tubes to which the complex composition of the luciferase GL2 expression-inhibiting siRNA with a liposome (Comparative Example 1), the complex compositions of Wnt1 expression-inhibiting siRNA with the liposome (Examples 3-1, 3-5 and 3-7), and the complex composition of two Wnt1 expression-inhibiting siRNAs with a cationic polymer polyethylenimine (Example 4-2) were then added, respectively. A final concentration of siRNA in the media was adjusted to 50 nM. These materials were slowly pipetted, mixed and allowed to stand at room temperature for 20 min, thus resulting in formation of a complex composition. The thus-prepared complex composition was added to the well plate, followed by cell culture in a $CO_2$ incubator at 37° C. 92 hours after treatment of the cells with individual complex compositions, the cultured cells of the plate were washed with PBS, and stained for 1 min with treatment of 500 µl of a solution containing 0.5% crystal violet and 20% methanol, followed by removal of the solution and observation of the residual cells on the plate. Non-siRNA treated cells were used as a control group.

Figure 5:
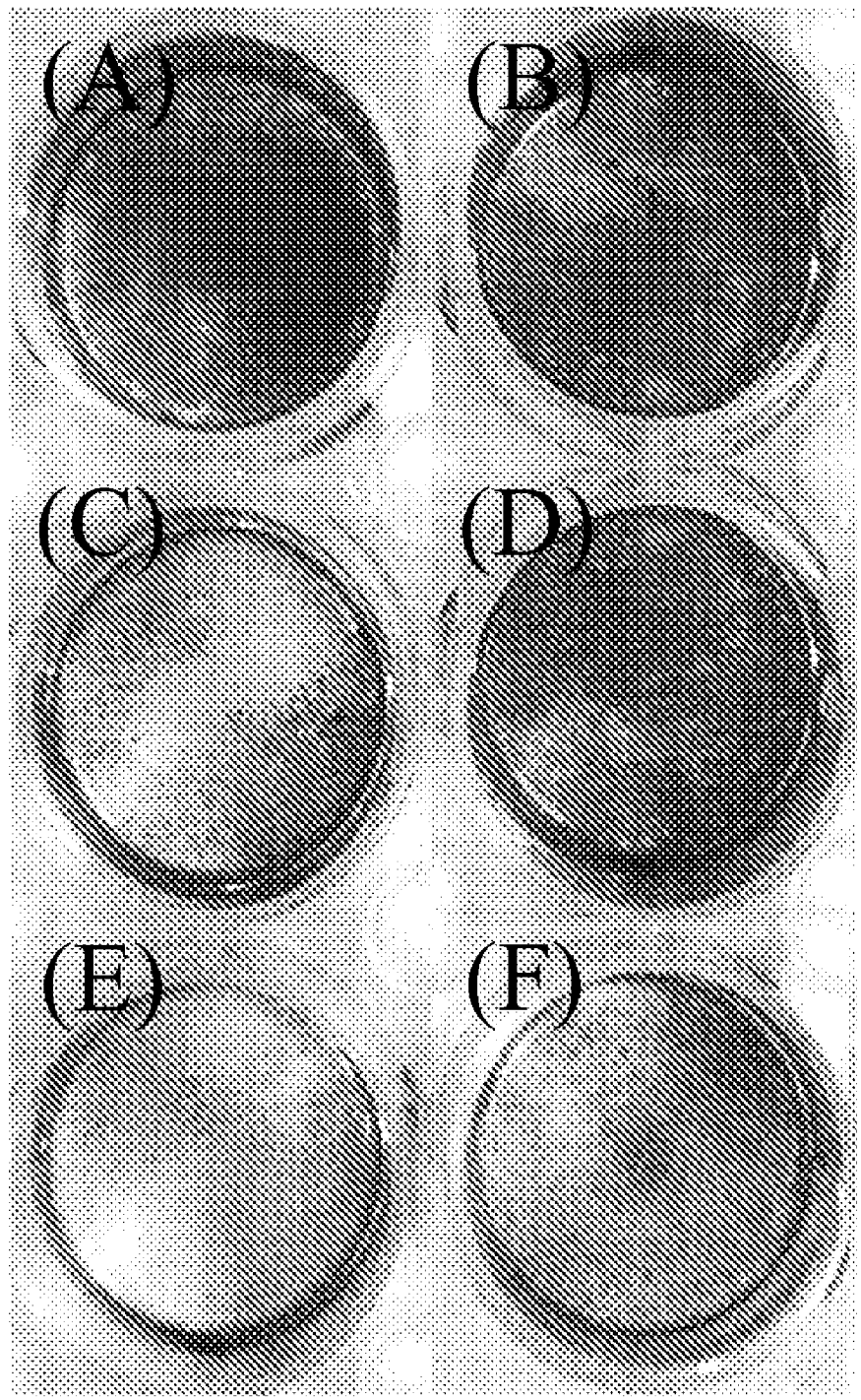
FIG. 5 shows the results confirming apoptotic effects of Wnt1 expression-inhibiting siRNA in the human hepatoma cell line Hep3B, via a cell staining method using a crystal violet dye.

FIG. 5 shows the assay results confirming apoptotic effects of Wnt1 expression-inhibiting siRNA in the human hepatoma cell line Hep3B, by the cell staining method using a crystal violet dye. The cells were treated as follows. A: Control; B: Complex of Comparative Example 1, C: Complex of Example 3-2; D: Complex of Example 3-5 having no Wnt1 expression-inhibitory ability, E: Complex of Example 3-7, and F: Complex of Example 4-2. When compared with the non-RNA treated control group (FIG. 5A) and the group treated with the complex of Comparative Example 1 (FIG. 5B), the group treated with the siRNA/liposome complex of Example 3-5 having no Wnt1 expression-inhibitory ability (FIG. 5D) exhibited staining of great numbers of the residual cells adherent to the well plate, thus representing no significant difference in apoptotic cell death. On the other hand, the cell groups treated with the composition of Example 3-2, the composition of Example 3-7, and the composition of Example 4-2 (FIGS. 5C, 5E and 5F), which had exhibited the inhibition of Wnt1 expression in Example 5, exhibited a decreased proportion of stained residual cells because damaged tumor cells were detached from the well plate. Therefore, it can be seen through FIG. 5 that the siRNA/liposome compositions prepared in Examples 3-2 and 3-7 exhibited selective suppression of the Wnt1 expression, thereby providing antitumor effects. Further, as observed in the group treated with the complex composition of Examples 4-2, a combined use of two effective siRNAs can also exhibit significant antitumor effects.

What is claimed is:

1. A pharmaceutical composition comprising one or more small interfering RNAs (siRNAs) that are capable of inhibiting intracellular expression of Wnt1 through complementary binding to a Wnt1 transcript (mRNA transcript) base sequence as set forth in SEQ ID NO: 2.

2. The composition of claim 1, wherein the siRNA is a chemically modified form.

3. The composition of claim 1, which comprises the siRNA in the form of a complex with a nucleic acid delivery system.

4. The composition of claim 3, wherein the nucleic acid delivery system is a cationic liposome.

5. The composition of claim 4, wherein the cationic liposome includes at least one cationic lipid selected from the group consisting of 1,2-dioleoyl-sn-glycero-3-ethylphosphocholine (EDOPO), 1-palmitoyl-2-oleoyl-sn-glycero-3-ethylphosphocholine (EPOPO), 1,2-dimyristoyl-sn-glycero-3-ethylphosphocholine (EDMPC), 1,2-distearoyl-sn-glycero-3-ethylphosphocholine (SPC), 1,2-dipalmitoyl-sn-glycero-3-ethylphosphocholine (EDPPC), 1,2-dioleoyl-3-trimethylammonium-propane (DOTAP), N-[1-(2,3-dioleyloxy)propyl]-N,N,N-trimethylammonium chloride (DOTMA) and 3β-[N-(N',N'-dimethylaminoethane)-carbamoyl]cholesterol (DC-Cholesterol).

6. The composition of claim 5, wherein the cationic liposome further includes at least one auxiliary lipid selected from the group consisting of 1,2-diacyl-sn-glycero-3-phosphoethanolamine (DOPE), 1,2-diphytanoyl-sn-glycero-3-phosphoethanolamine (DPhPE), 1,2-dioleoyl-sn-glycero-3-phosphocholine (DOPC), 1,2-dioleoyl-sn-glycero-3-[phospho-L-serine] (DOPS), 1,2-dioleoyl-sn-glycero-3-ethylphosphocholine (DO-Ethyl-PC), and cholesterol.

7. The composition of claim 3, wherein the nucleic acid delivery system is a cationic polymer.

8. The composition of claim 7, wherein the cationic polymer is selected from the group consisting of poly-L-lysine, poly-L-ornithine, poly-L-histidine, poly-L-arginine, bis(3-aminopropyl)terminated polytetrahydrofuran, polyacrylamide (PA), poly(α-[4-aminobutyl]-L-glycolic acid (PAGA), poly(2-aminoethyl propylene phosphate) (PPE-EA), cationic derivatives of cyclodextrin, poly(2-(dimethylamino)ethyl methacrylate (pDMAEMA), poly(4-vinylpyridine) (P4VP), O,O'-bis(2-aminopropyl)polypropylene glycol-block-polyethylene glycol-block-polypropylene glycol, chitosan, chitosan derivatives, polyethylenimine (PEI), polyethylenimine derivatives, polyamidoamine (PAMAM), fractured PAMAM and poly-N-ethyl-4-vinylpyridinium tribromide.

9. The composition of claim 1, further comprising a cancer chemotherapeutic agent.

10. The composition of claim 1, wherein the siRNA has a sense sequence of SEQ ID NO: 18 and an antisense sequence of SEQ ID NO: 19.

11. An siRNA inhibiting expression of Wnt1 and having a sense sequence of SEQ ID NO: 18 and an antisense sequence of SEQ ID NO: 19.

12. A method for treating cancer comprising administering to a subject in need thereof the composition of claim 1 in a pharmaceutically effective amount.

13. A method for treating cancer comprising administering to a subject in need thereof the siRNA of claim 11 in a pharmaceutically effective amount.

* * * * *